Figure 1:
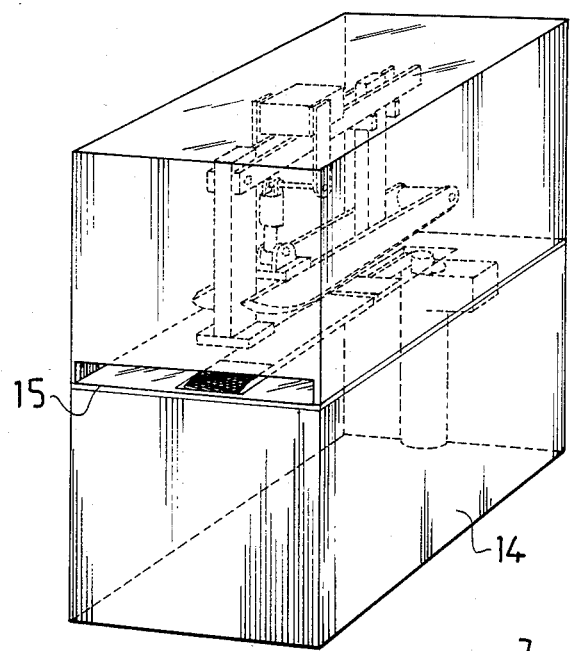

United States Patent [19]

Lehtikoski et al.

[11] Patent Number: 4,550,613

[45] Date of Patent: Nov. 5, 1985

[54] APPARATUS FOR AUTOMATIC DETERMINATION OF THE TENSILE STRENGTH PROPERTIES OF A SHEET OF PAPER

[76] Inventors: Olavi Lehtikoski, Sölvenkatu 8, SF-78300 Varkaus 30; Martti Nissinen, Kirvesniementie 2, SF-78880 Kuvansi, both of Finland

[21] Appl. No.: 560,829

[22] Filed: Dec. 13, 1983

[30] Foreign Application Priority Data

Dec. 30, 1982 [FI] Finland .................................. 824510

[51] Int. Cl.$^4$ .............................................. G01N 3/08
[52] U.S. Cl. ......................................... 73/834; 73/159
[58] Field of Search ................... 73/834, 831, 159, 833

[56] References Cited

U.S. PATENT DOCUMENTS

| | | | |
|---|---|---|---|
| 662,327 | 11/1900 | Vermilye | 73/834 |
| 3,537,301 | 11/1970 | Hasenwinkle | 73/834 |
| 3,838,596 | 10/1974 | Neuenschwander | 73/834 |

*Primary Examiner*—Anthony V. Ciarlante

*Attorney, Agent, or Firm*—Cohen, Pontani & Lieberman

[57] ABSTRACT

The present-day devices for automatic determination of the tensile strength properties of a sheet of paper are complicated, inconvenient to operate and incapable of producing immediate test results. According to the invention, the apparatus comprises two operating elements (6, 7) between which a sheet of paper of desired length is adapted to be introduced, the former operating element (6) comprising a fixing block (1) and a pulling block (2) and the latter operating element (7) comprising a fixing head (3) and a pulling head (4), said fixing head being compressible against the fixing block and said pulling head being compressible against the pulling block for fastening a sheet of paper. The other operating element is further fitted with a cutter means (8) which is adapted cut off a sheet of paper a sample of standard width as the sheet is positioned against the fixing block. The apparatus is further provided with a measuring device (5) for determining the displacement of said pulling block and for measuring the tensile strength properties of paper.

3 Claims, 2 Drawing Figures

U.S. Patent

Nov. 5, 1985

4,550,613

APPARATUS FOR AUTOMATIC DETERMINATION OF THE TENSILE STRENGTH PROPERTIES OF A SHEET OF PAPER

It has been known in the art to automatically determine the tensile properties of paper, such as tensile strength, break elongation and tensile load. The present-day equipment is however structurally complicated and a sample must be shuffled in such assemblies from station to station which is inconvenient, increases testing time and may lead to damage to the sample being tested. Furthermore, due to their complicated designs, the present assemblies must be fixedly mounted in separate laboratory rooms, which means that considerable amount of time always passes between sampling and measuring and the properties of a sample have time to change.

An object of the invention is to provide an apparatus for automatic determination of the tensile strength properties of a sheet of paper, which apparatus eliminates drawbacks of today's assemblies. A particular object of the invention is to provide an apparatus, wherein a sample of paper need not be shifted during tests. Another object of the invention is to provide an apparatus which is simple and easy to operate and accelerates measuring of tensile strength properties as compared to the prior art equipment.

This object of the invention is accomplished by means of an appratus which is substantially characterized by what is set forth in the annexed claims.

By means of the apparatus of the invention the tensile properties of a sheet paper inserted in said apparatus can be measured very quickly and the test results are available for use immediately after testing. The apparatus comprises a simple transportable testing device which can be readily carried to a desired location, e.g. directly to the location of paper making process. The apparatus may also be positioned in a transportable air-conditioned minilaboratory which also includes test units for testing other desired properties. Thus, a conveyor or the like fitted in the minilaboratory carries a material to be tested to the apparatus and the test results are printed out by means of the output unit of said minilaboratory. When the apparatus is used as a separate unit, a material to be tested is introduced into the apparatus e.g. manually and test results are printed out by a separate output device.

Figure 2:
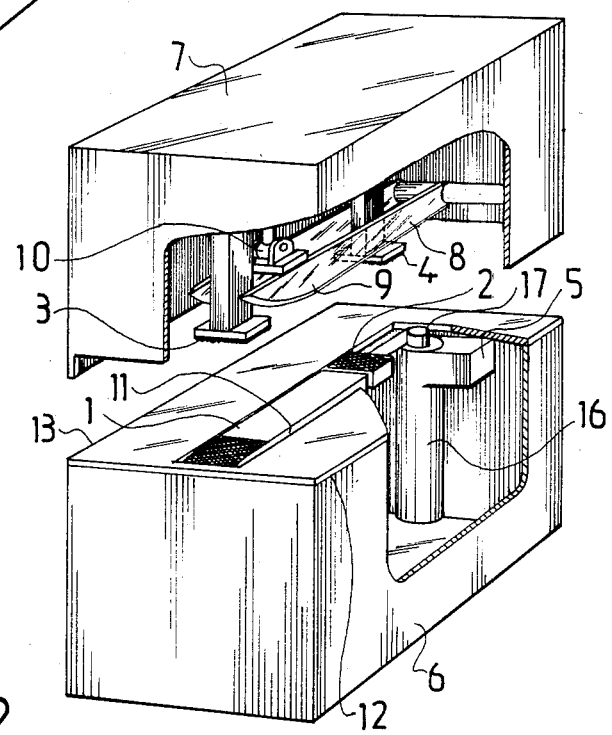

The invention will now be described in more detail with reference made to the accompanying drawing, in which FIG. 1 shows an apparatus of the invention viewed obliquely in side view, and FIG. 2 is an obliquely viewed side view in partial section of the internal elements of an apparatus of the invention.

The apparatus shown in FIG. 1 comprises a housing 14 provided with an inlet slot 15 for introducing a sheet of paper in the device. On the side opposite to said inlet there is provided an outlet slot (not shown in figure) for paper.

The apparatus shown in FIG. 2 comprises a flat fixing block 1 and a flat pulling block 2, the latter being displaceable relative to said fixing block in the same plane a fixing head 3 squeezable against the fixing block for securing a sheet of paper, a pulling head 4 squeezable against the pulling block for fixing a sheet of paper, pulling head being adapted to travel along with the pulling block, a measuring device 5 for measuring the tensile strength properties of paper and a motor 16 for driving the pulling block. The apparatus further comprises two operating elements 6, 7 mounted on the housing shown in FIG. 1, the former operating element 6 being provided with fixing block 1 and pulling block 2 and the latter operating element 7 being provided with fixing head 3 and pulling head 4 and, in this embodiment, also with a cutter means 8. A sample of paper is adapted to be fixed between these two operating elements and the cutter means is adapted to cut a sheet of paper into a sample blank of standard width as the sheet is positioned against the fixing block.

In this special embodiment, the cutter means 8 is comprised of two parallel, spaced apart blades 9 extending in the direction of said fixing block, as well as a drive means 10 mounted on the blades for urging said blades towards said fixing block for cutting a sample blank. The fixing block is of elongated shape, uniform in width and extends in the direction of the blades of said cutter means and makes up two edges 11, spaced at a standard distance from each other and extending in the direction of said pulling head. The fixing block and pulling block are positioned substantially centrally of the operating element at a distance from the sides 12, 13 of said operating element.

When testing a sample, a sheet of paper is introduced between operating elements 6 and 7. When the apparatus is positioned e.g. in a minilaboratory, the conveyor of said laboratory will carry the sheet of paper to a desired location while, if the assembly is working as a separate unit, the apparatus can be provided with a separate conveyor or paper can be introduced in the device e.g. manually. Blades 9 are used to cut a sample blank to a determined format off said sheet of paper by using drive means 10 to press the blades towards the fixing block, the blades cutting off said sheet of paper a sample blank as they pass along and up against the fixing block edges 11. The cut-out blank is secured to the fixing block by compressing fixing head 3 against the fixing block and to the pulling block 2 by compressing pulling head 4 up against pulling block. The cutter blades are lifted up and drive motor 16 actuated. The drive motor sets the pulling block in motion and the pulling head travels along with said pulling block continuously pressing a sample blank against the pulling block. Operating element 7 is provided with a guide (not shown in figure) to which the pulling head rod is adapted to be supported as said pulling head travels along with the pulling block. During the pulling action, the tensile strength properties of a sample blank are continuously measured and the blank is pulled until it breaks. After the blank is broken, the displaceable pulling block and pulling head are returned to their intial position. The tested (and broken) specimen is removed and a new sheet of paper is shifted into the apparatus and a new test is performed in the similar sequence.

By means of a measuring device 5, the tensile strength properties of paper are measured on the basis of the displacement of pulling head. Measuring can be effected e.g. by means of resistance elongation strips, the elongation being measured by means of an electric sensor which measures changing of the angle of roll of a drive shaft 17 but it is also possible to use other solutions known in the art for measuring displacement of a pulling block.

The invention has been described above with reference to one preferred embodiment but also other embodiments and modifications are possible within the scope of the inventive idea defined in the annexed claims.

We claim:

1. Apparatus for the automatic determination of the tensile strength properties of a sheet of paper, said apparatus comprising a substantially flat fixing block of predetermined and uniform width and a pulling block which is displaceable relative to the fixing block in the same plane, a fixing head pressable against the fixing block for holding a sheet of paper therebetween, a pulling head pressable against the pulling block for holding a sheet of paper therebetween, said pulling head being movable along with the pulling block, a measuring device for measuring the tensile strength properties of paper, a cutter means adapted to cut off said sheet of paper a sample blank of standard width as the sheet is positioned between and pressed by the fixing block and fixing head at one end of said sample blank and between and pressed by said pulling block and said pulling head at the other end of said sample blank, said cutter means comprising two parallel blades spaced apart by said width of said fixing block and extending in the direction of said fixing block on opposite sides of said fixing head and said pulling head, and drive means mounted on the blades for pushing said blades towards the two longitudinal sides of the fixing block for cutting a sample blank of said predetermined width.

2. The apparatus of claim 1, wherein said pulling head and said pulling block are of a width no greater than said predetermined width and which are disposed between said blades.

3. The apparatus of claim 2, said apparatus further comprising first and second operating elements movable toward and away from one another in a direction perpendicular to the plane of said fixing block, said fixing block and said pulling block being supported by said first operating element, said fixing head, said pulling head and said blades being supported by said second operating element.

* * * * *